(12) United States Patent
Lepape et al.

(10) Patent No.: US 9,278,143 B2
(45) Date of Patent: Mar. 8, 2016

(54) IMAGING AGENTS, PROCESS FOR THE PREPARATION THEREOF AND PHARMACEUTICAL COMPOSITIONS CONTAINING SAME

(75) Inventors: Alain Lepape, Lignieres de Touraine (FR); Stéphanie Lerondel, Orleans (FR); Guillaume Reveillon, Orsay (FR); Jean-Marie Delbos, Romorantin Lanthenay (FR); Luc Demuynck, Orleans (FR); Hubert Grandon, Orleans (FR); François Lefoulon, Orleans (FR); Gordon Tucker, Paris (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 74 days.

(21) Appl. No.: 14/232,163

(22) PCT Filed: Jul. 12, 2012

(86) PCT No.: PCT/FR2012/051667
§ 371 (c)(1),
(2), (4) Date: May 9, 2014

(87) PCT Pub. No.: WO2013/007959
PCT Pub. Date: Jan. 17, 2013

(65) Prior Publication Data
US 2014/0241989 A1     Aug. 28, 2014

(30) Foreign Application Priority Data
Jul. 13, 2011   (FR) ...................................... 11 02213

(51) Int. Cl.
| | |
|---|---|
| *A61K 49/00* | (2006.01) |
| *C07D 401/12* | (2006.01) |
| *C07D 209/60* | (2006.01) |
| *C07D 213/74* | (2006.01) |
| *C07D 401/14* | (2006.01) |
| *C07D 493/10* | (2006.01) |

(52) U.S. Cl.
CPC .......... *A61K 49/0004* (2013.01); *C07D 209/60* (2013.01); *C07D 213/74* (2013.01); *C07D 401/12* (2013.01); *C07D 401/14* (2013.01); *C07D 493/10* (2013.01)

(58) Field of Classification Search
CPC .... A61K 49/00; C07D 213/74; C07D 401/12; C07D 401/14; C07D 493/10
USPC .......................................... 424/9.1, 9.2, 9.3
See application file for complete search history.

(56) References Cited

U.S. PATENT DOCUMENTS

| | | | |
|---|---|---|---|
| 6,558,649 B1 | 5/2003 | Cheesman et al. | |
| 6,818,201 B2 | 11/2004 | Cheesman et al. | |

FOREIGN PATENT DOCUMENTS

WO    WO 2009/114776 A2    9/2009

OTHER PUBLICATIONS

Xiaoyuan Chen et al., Integrin Targeting for Tumor Optical Imaging, Theronostics, 1, 102-126, 2011.*
Albelda et al., "Integrin Distribution in Malignant Melanoma: Association of the $\beta_3$ subunit with Tumor Progession", Cancer Res, vol. 50, Oct. 15, 1990 (http://cancerres.aacrjournals.org/content/50/20/6757), pp. 6757-6764.
Bachmann et al,, "Tumor necrosis is associated with increased $\alpha v\beta 3$ integrin expression and poor prognosis in nodular cutaneous melanomas", BMC Cancer, vol. 8, Dec. 5, 2008 (Published online: http://www.biomedcentral.com/1471-2407/8/362), 10 pages.
Bello et al., "$\alpha v\beta 3$ and $\alpha v\beta 5$ Integrin Expression in Glioma Periphery", Neurosurgery, vol. 49, No. 2, Aug. 2001, pp. 380-390.
Brooks et al., "Requirement of Vascular Integrin $\alpha v\beta 3$ for Angiogenesis,"Science, vol. 264, Apr. 22, 1994, pp. 569-571.
Felding-Habermann et al., "Integrin activation controls metastasis in human breast cancer", PNAS, vol. 98, No. 4, Feb. 13, 2001, pp. 1853-1858.
French language International Search Report and partial English translation thereof (forms PCT/IB/301, PCT/IB/304, PCT/IB/308, PCT/IB/311 and PCT/ISA/210), dated Aug. 31, 2012, for International Application No. PCT/FR2012/051667.
Gasparini et al., "Vascular integrin $\alpha v\beta$: a new prognostic indicator in breast cancer", Clin Cancer Res, vol. 4, Nov. 1998, pp. 2625-2634.
Gladson et al., "Glioblastoma Expression of Vitronectin and the $\alpha v\beta 3$ Integrin Adhesion Mechanism for Transformed Glial Cells", J. Clin. Invest., vol. 88, Dec. 1991, pp. 1924-1932.
Kossodo et al., "Dual In Vivo Quantification of Integrin-targeted and Protease-activated Agents in Cancer Using Fluorescence Molecular Tomography (FMT)", Mol Imaging Biol., vol. 12, 2010 (Published Online: Dec. 4, 2009), pp. 488-499.
Lafrenie et al., "The Relative Roles of Vitronectin Receptor, E-selectin and $\alpha_4\beta_1$ in Cancer Cell Adhesion to Interleukin-1-treated Endothelial Cells", European Journal of Cancer, vol. 30A, No. 14, 1994, pp. 2151-2158.
Landen et al., "Tumor-Selective Response to Antibody-Mediated Targeting of $\alpha v\beta 3$ Integrin in Ovarian Cancer", Neoplasia, vol. 10, No. 11, Nov. 2008, pp. 1259-1267.
Paganin-Gioanni et al., "Fluorescence Imaging of Small Animal: Visualization of molecular and cellular events within the live animal", STAL, vol. 35, 2009, pp. 49-55.
Wayner et al., "Integrins $\alpha v\beta 3$ and $\alpha v\beta 5$ Contribute to Cell Attachment to Vitronectin but Differentially Distribute on the Cell Surface", The Journal of Cell Biology, vol. 113, No. 4, May 15, 1991, pp. 919-929.
Ye et al., "Integrin Targeting for Tumor Optical Imaging", Theranostics, vol. 1, Feb. 1, 2011, pp. 102-126.
International Search Report issued in PCT/FR2012/051667, mailed on Aug. 31, 2012.

* cited by examiner

*Primary Examiner* — Michael G Hartley
*Assistant Examiner* — Jagadishwar Samala
(74) *Attorney, Agent, or Firm* — Birch, Stewart, Kolasch & Birch, LLP

(57) ABSTRACT

Compounds of formula (I) in which: >R is a linear or branched ($C_1$-$C_6$) alkyl, >L is a spacer group, >A is a diagnostic agent, and >m is equal to 1 or 2.

17 Claims, 7 Drawing Sheets

IMAGING AGENTS, PROCESS FOR THE PREPARATION THEREOF AND PHARMACEUTICAL COMPOSITIONS CONTAINING SAME

The present invention relates to novel imaging agents, the process for the preparation thereof, and pharmaceutical compositions containing same and use thereof for diagnostic purposes.

Current approaches of molecular diagnosis of a given disease generally require blood and tissue samples, surgery, or, in the case of animal experiments, sacrifices. A recent development, the direct imaging of living cells has become a fundamental tool to study biological processes in real-time, non-invasively, directly within a living organism. For example, fluorescence optical imaging provides functional data in real-time in in vivo tumor models (Pagani-Gioanni et al., *STAL* 2009, 36, 41-47).

Use of targeted molecular probes for in vivo imaging involves use of an agent that selectively targets a gene, protein, receptor or cellular function, which are the specific targets of a particular stage of the evolution of pathology. This imaging technique enables the measurement and/or visualization of target molecules and molecular pathways in vivo while providing information on physiopathological processes at the molecular level.

Integrins are transmembrane cell adhesion receptors located on the cell's surface which bind to molecules of the extracellular matrix. Once the receptor is activated, a cascade of intracellular signals is activated causing various biological phenomena such as cell growth, survival, differentiation and apoptosis.

Structurally, integrins are heterodimeric proteins composed of an α subunit and a β subunit. To date, 18 different α subunits and 8 different β subunits exist, and the combination thereof determines the specificity of the integrin to the ligand. Among the various possible combinations, $\alpha_v$, $\alpha_5\beta_1$ and $\alpha_{IIb}\beta_3$ integrins are distinguished, which recognize the arginine-glycine-aspartic acid (RGD) sequence of extracellular matrix proteins. Vitronectin receptors $\alpha_v\beta_3$ and $\alpha_v\beta_5$, as well as fibronectin receptor $\alpha_5\beta_1$ regulate the migration and adhesion of cancer cells via the RGD sequence (Albelda et al., *Cancer Res.* 1990, 50, 6757-64; Gladson et al., *J Clin. Invest.* 1991, 88, 1924-32; Lafrenie et al., *Eur. J. Cancer* 1994, 30, 2151-58). In particular, $\alpha_v\beta_3$ and $\alpha_v\beta_5$ integrins are expressed in many tumor cells such as glioblastoma (Bello et al., *Neurosurgery* 2001, 49, 380-9), melanoma (Albelda et al., *Cancer Res.* 1990, 50, 6757-64) and carcinomas of breast (Felding-Habermann et al., *PNAS* 2001, 98, 1853-8), lung (Wayner et al., *J. Cell Biol.* 1991, 113, 919-29) and ovaries (Landen et al., *Neoplasia* 2008, 10, 1259-67).

Angiogenesis is a normal physiological process describing the growth of new blood vessels (neovascularization) from preexisting vessels. It occurs during embryonic development and tissue repair but also in the growth of malignant tumors and the development of metastases. In particular, $\alpha_v\beta_3$ and $\alpha_v\beta_5$ integrins are strongly expressed in activated endothelial cells during tumor neovascularization but relatively absent in quiescent endothelial cells and in most healthy tissues (Brooks et al., *Science* 1994, 264, 569-71). Lastly, clinical observations have shown a direct correlation between integrin expression rates and tumor progression (Gasparini et al., *Clin. Cancer Res.* 1998, 4, 2625-34; Bachmann et al., *BMC Cancer* 2008, 8, 362). Consequently, $\alpha_v\beta_3$ and $\alpha_v\beta_5$ integrins are an attractive target in the detection of tumor and metastatic growth.

It appears from the above that imaging techniques capable of specifically locating the molecular target could significantly improve the practitioner's ability to diagnose and determine an effective treatment according to the stage of evolution of the disease (from the early development of a primary tumor until the appearance of metastases). They would make it possible to evaluate the antitumor effects of a drug in efficacy studies or to guide the surgeon by intraoperative imaging during tumor resection.

In the literature, agents used for fluorescence optical imaging specifically targeting integrins have been developed (WO 2009/114776; Kossodo et al., *Mol. Imaging Biol.* 2010, 12, 488-99; Ye et al., *Theranostics* 2011, 1, 102-26). Other imaging agents comprising a radioisotope have also been described (U.S. Pat. No. 6,818,201).

Despite real progress in noninvasive imaging, methods and imaging agents that are more sensitive and more specific are still necessary. In particular, it is advantageous to have probes able to detect a broader spectrum of tumor types, to improve the contrast between the tumor zone and non-specific sites, and to minimize accumulation in healthy tissues.

The compounds of the invention, beyond the fact that they are novel, relate to imaging agents with advantageous pharmacological characteristics conferring to them properties that make them useful in the diagnostic imaging of hard to detect cancers and in situations where the tumor environment complicates precise discrimination between healthy tissue and tumor structures. It is a matter in particular of deep thoracic and abdominal areas and areas having tissue or vascular background noise in intraoperative imaging or fibroscopic imaging.

More specifically, the present invention relates to compounds of formula (I):

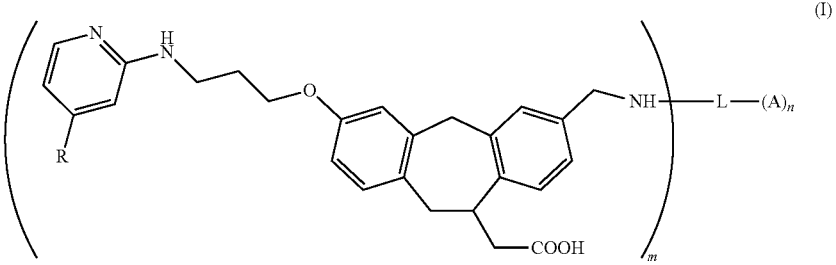

wherein:
R is a linear or branched ($C_1$-$C_6$) alkyl group;
L is a spacer group;
A is a diagnostic agent;
m and n are each independently equal to 1 or 2;

enantiomers thereof, diastereoisomers thereof, as well as pharmaceutically acceptable acid or base addition salts thereof.

Among the pharmaceutically acceptable acids, mention may be made, without limitation, of hydrochloric, hydrobromic, sulfuric, acetic, trifluoroacetic, lactic, malonic, succinic, glutamic, fumaric, maleic, phosphoric, citric, oxalic, methane sulfonic, benzene sulfonic, para-toluenesulfonic, camphoric acids, etc.

Among the pharmaceutically acceptable bases, mention may be made, without limitation, of sodium hydroxide, potassium hydroxide, triethylamine, tert-butylamine, etc.

By targeting ligand is meant the following compound of formula (II):

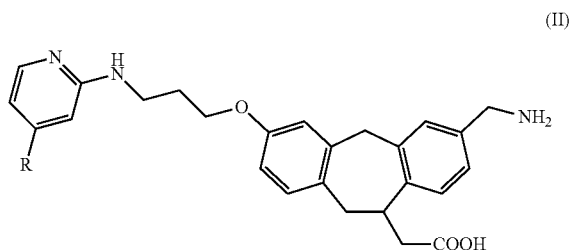

(II)

wherein R is as defined in formula (I).

More particularly, the targeting ligand is (7-(aminomethyl)-3-{3-[(4-methyl-2-pyridinyl)amino]propoxy}-10,11-dihydro-5H-dibenzo[a,d]cyclohepten-10-yl)acetic acid.

In the compounds of formula (I), R is preferentially a methyl group.

By spacer group is meant a functionalized molecular group used to covalently chemically bond one or more targeting ligands to one or more identical or different diagnostic agents.

Generally, the spacer group L of the present invention is a $C_1$-$C_{20}$ saturated or unsaturated, linear or branched hydrocarbon chain, given that:
 one or more methylene groups can also be replaced by an oxygen atom; a —NH— group; a —CO— group; a hydroxy group; a phenyl group; or a pyridyl group and said hydrocarbon chain forms a —NH—CO— peptide bond with the primary amine of the targeting ligand.

According to a particular embodiment of the invention, L can be a derivative of a non-cyclic, natural or non-natural amino acid, given that the acid functional group of said amino acid located on the α carbon and/or the side chain, if it exists, forms a peptide bond with the primary amine of the targeting ligand.

Preferentially, the spacer group L is a —CO— group; a ($C_1$-$C_6$) alkylcarbonyl group; a phenylcarbonyl group; or a pyridylcarbonyl group.

According to a preferred embodiment, L is the n-pentylcarbonyl group.

According to another advantageous embodiment, the spacer group L is a 6-aminocaproic acid derivative, and more particularly the —CO—$(CH_2)_5$—NH— group; a glutamic acid derivative, and more particularly the

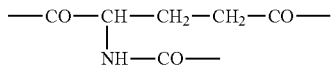

group; or a lysine derivative, and more particularly the

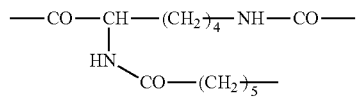

group.

By diagnostic agent is meant a chemical entity detectable by nuclear medicine (scintigraphy, for example), fluorescence, radioactivity or optical detection, allowing the visualization of an anatomical structure (an organ, for example) or a pathological structure (a tumor, for example) that is difficult to distinguish from nearby tissues. Among the available chemical entities envisaged as diagnostic agent, a radioactive marker, a paramagnetic metal ion, a fluorophore or a nanoparticle (commonly called a quantum dot) will be preferentially selected.

By radioactive marker is meant any atom that has an unstable and radioactive nucleus (radioisotope) of metals such as copper, indium or technetium, or radioisotopes of halogen atoms such as iodine or fluorine. Among the radioisotopes of the elements above, mention may be made, for example, of $^{64}$Cu, $^{67}$Cu, $^{111}$In, $^{99m}$Tc, $^{123}$I, $^{125}$I, $^{18}$F, etc.

By paramagnetic metal ion is meant an ion of a transition metal that does not possess spontaneous magnetization but that, under the effect of an external magnetic field, acquires magnetization directed in the same direction as this excitatory field. Among these metal ions, mention may be made, for example, of Gd(III), Mn(II), Fe(III), etc.

The radioactive metal markers and paramagnetic metal ions are bound to the imaging agent by chelation using a chelator.

By chelator is meant an entity bound covalently to the imaging agent at the spacer group and likely to fix by chelation a radioisotope or a paramagnetic metal ion. Among the chelators capable of forming stable complexes with metal cations, mention may be made, without limitation, of diamine-dithiols, triamide-monothiols, diamine-dioximes, hydrazines, polyaminocarboxylic acids (DTPA, DOTA, etc.), etc.

By fluorophore is meant any chemical substance capable of emitting fluorescent light after excitation. Among the commercially available fluorophores useful in the design of the imaging agents of the present invention, mention may be made, without limitation, of fluorescein; cyanines Cy™ 3, Cy™ 5, Cy™ 5.5 and Cy™ 7 (GE Healthcare); Alexa Fluor® 660, Alexa Fluor® 680, Alexa Fluor® 750 and Alexa Fluor® 790 (Invitrogen); VivoTag® 680, VivoTag-S® 680 and VivoTag-S® 750 (VisEn Medical); Dy™ 677, Dy™ 682, Dy™ 752 and Dy™ 780 (Dyomics); DyLight® 547 and DyLight® 647 (Pierce); etc.

Advantageously, the compounds of formula (I) are the compounds for which A is a fluorophore. Group A is preferentially fluorescein, Alexa Fluor® 750, Cy™ 3, Cy™ 5.5 or Cy™ 7. More particularly, the preferred fluorophore is Cy™ 5.5.

Preferred compounds of the invention are those for which A is a radioisotope of iodine suitable for the imaging modality envisaged: $^{123}$I for scintigraphy, $^{124}$I for positron emission tomography, or $^{125}$I for small animal imaging.

Another preferred possibility for the compounds of formula (I) is when A is the hydrazine group associated with the radioisotope $^{99m}$Tc.

According to a first preferred embodiment, m and n are equal to 1.

An advantageous embodiment is when m is equal to 1 and n is equal to 2. In this latter embodiment, the diagnostic agents are preferentially different. In particular, a first diagnostic agent represented by a fluorophore and a second agent represented by a radioisotope associated with a chelator will be selected.

The preferred compounds of the invention are the compounds represented by the following formulas:

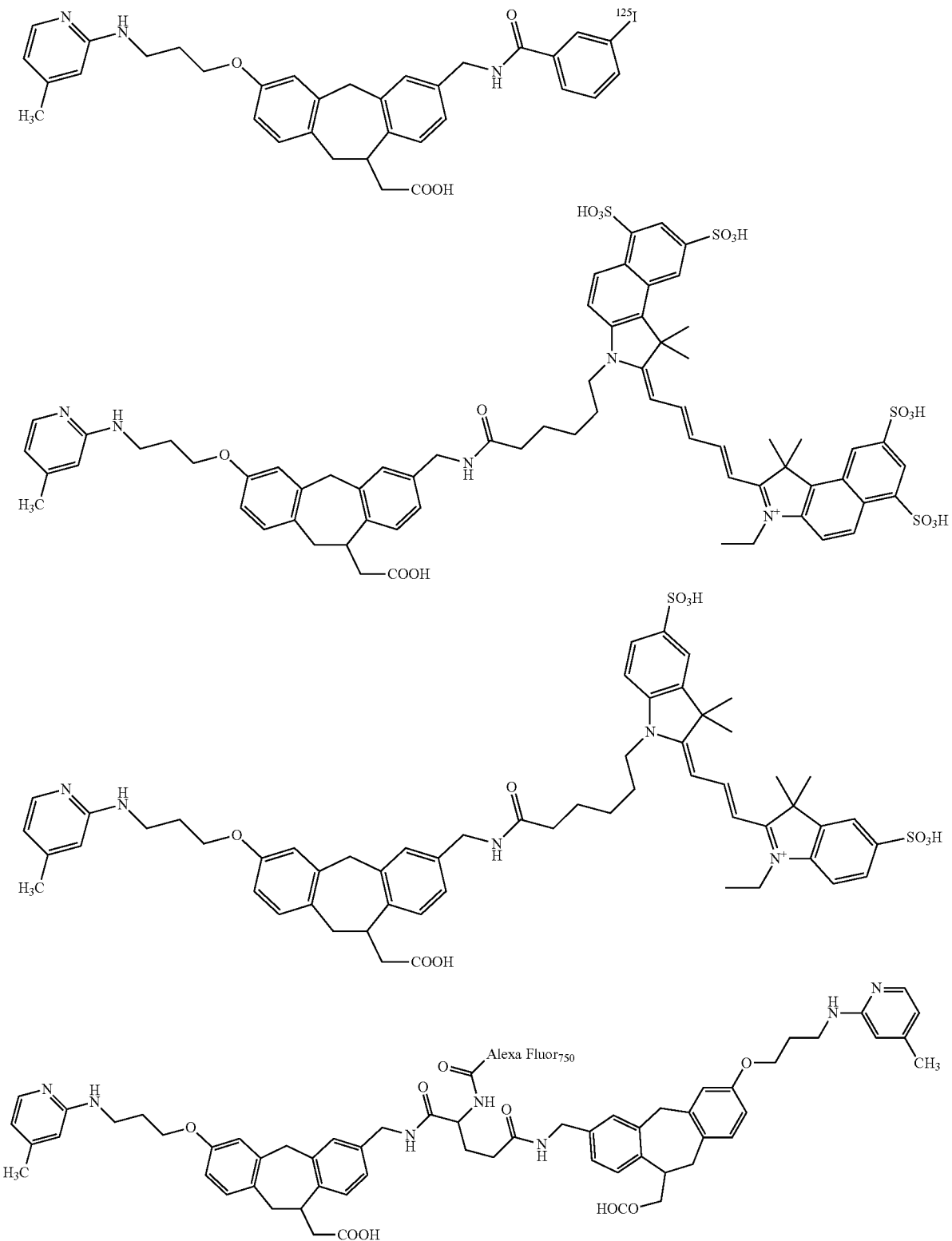

The pharmaceutically acceptable acid or base addition salts of the preferred compounds of the invention are an integral part of the invention.

The invention also extends to the process for the preparation of the compounds of formula (I), characterized in that the starting product used is a compound of formula (II):

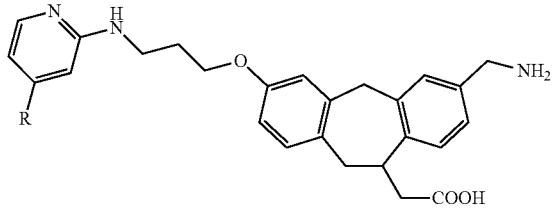

(II)

wherein R is as defined in formula (I),
which is reacted with a compound of formula (III):

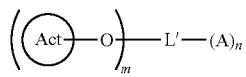

(III)

wherein
A, m and n are as defined in formula (I);
Act is a peptide coupling activator such as N-hydroxysuccinimide (NHS), ethyl(dimethylaminopropyl)carbodiimide (EDC) or hydroxybenzothiazole (HOBt);
L' is a $C_1$-$C_{20}$ saturated or unsaturated, linear or branched hydrocarbon chain, given that:
one or more methylene groups can also be replaced by an oxygen atom; a —NH— group; a —CO— group; a hydroxy group; a phenyl group; or a pyridine group; and
the hydrocarbon chain forms an ester bond with the activator Act;
to lead to the compound of formula (I),
compound of formula (I) which can then be purified according to a standard separation technique.

The compounds of formula (III) are available commercially or are easily accessible to persons skilled in the art by standard chemical reactions or those described in the literature.

The compound of formula (II) is novel and is also part of the invention as an integrin receptor targeting ligand useful in the preparation of compounds of formula (I).

The compounds of formula (I) according to the invention are useful as a novel imaging agent for evaluating the function of organs or tumor zones.

Also within the scope of the present invention is the use of the compound of formula (I) to evaluate the effects of the administration of a drug to an animal or human suffering from a pathology during which neovascularization occurs.

The adjustment of the adequate effective quantities of the compound of formula (I) for implementation in a use according to the invention depends on the phenomenon or the entity to be detected and quantified. In vivo, the effective quantities can also be adjusted according to the size and weight of the individual to whom the use according to the invention is implemented, as well as according to the organ, tissue or cells targeted. The adjustments can be carried out by all methods typically practiced by persons skilled in the art.

In the sense of the present invention, "effective quantity" means the quantity necessary and sufficient to obtain the desired effect, namely the detection and/or quantification of a biological entity or a chemical, physical or biological phenomenon.

In the context of its implementation in vivo or in vitro, the compound of formula (I) can be formulated in order to be suitable for oral administration or parenteral administration, in particular intravenous, intra-arterial, intracardiac, intracerebroventricular, intraperitoneal or intratumoral administration, or for pulmonary, nasal or ophthalmic administration and possibly rectal, vaginal or topical administration.

The invention also extends to pharmaceutical compositions containing as active ingredient at least one compound of formula (I) alone or in combination with one or more non-toxic inert excipients or carriers. The compound of formula (I) can thus be implemented in a pharmaceutical composition suitable for the detection process to be carried out and the route of administration selected.

The compound of formula (I) of the invention can be administered to a living being, such as, for example, an animal or a human being, and then the detection of the marker can be carried out in vivo by means usually implemented in the field.

According to another embodiment, the present invention relates to a kit for preparing an imaging agent including at least one compound of formula (I) wherein A is, in particular, a radioisotope associated with a chelator. In this case, the kit includes one or more sealed containers containing a predetermined quantity of an imaging agent comprising said chelator. According to a certain embodiment, the kit can comprise a second sealed container containing a radioactive marker.

The kit can also contain conventional pharmaceutical adjuvants such as pharmaceutically acceptable salts to adjust osmotic pressure, buffers, preservatives, diluents, emulsifiers, excipients, etc.

The kit can in particular be a ready-to-use marking kit for teams working on experimental models of a given pathology.

The examples and figures presented below illustrate the invention and do not limit it in any way. The structures of the described compounds were confirmed by the usual spectroscopic techniques: NMR of the proton (s=singlet; bs=broad singlet; vbs=very broad singlet; d=doublet; bd=broad doublet; t=triplet; bt=broad triplet; dd=double doublet; q=quadruplet; bq=broad quadruplet; qt=quintuplet; bqt=broad quintuplet; m=multiplet; 2s=2 singlets; 2d=2 doublets); electron impact (EI) or electrospray ionization (ESI) mass spectrometry.

PREPARATION 1

Figure 1:
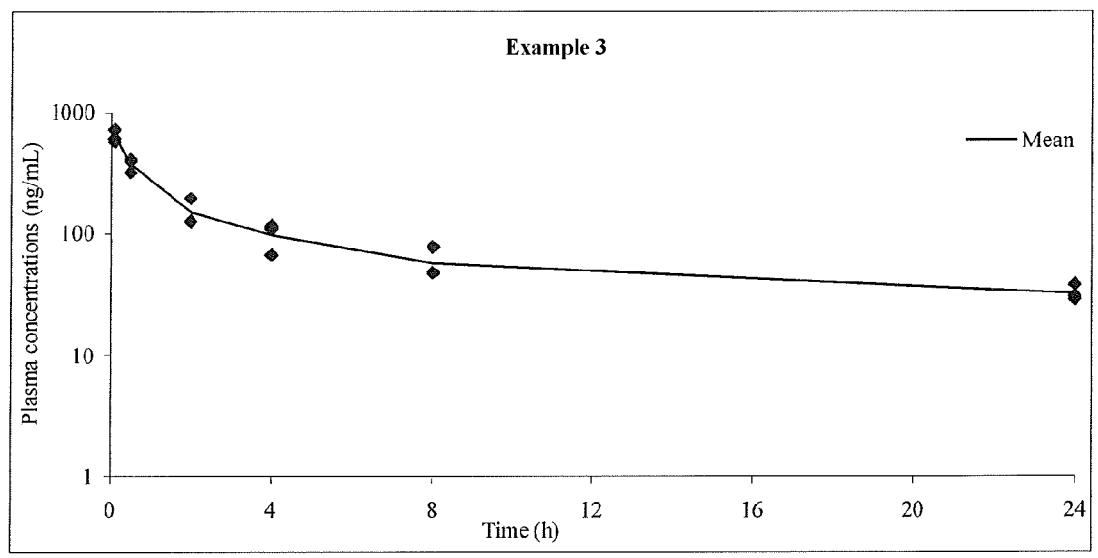
FIG. 1: Kinetics of the average plasma concentration (ng/ml) after intravenous injection of the compound of Example 3 (2 nmol/animal) in Swiss nude mice.

(7-(aminomethyl)-3-{3-[(4-methyl-2-pyridinyl) amino]propoxy}-10,11-dihydro-5H-dibenzo[a,d] cyclohepten-10-yl)acetic acid

Stage A: 3-(3-bromophenyl)-1H-inden-5-yl methyl ether

To a solution of 1-bromo-3-iodobenzene (339 mmol) in 600 ml of anhydrous THF at −40° C. is added dropwise a 1 M n-dibutylmagnesium solution in heptane (185 mmol). 6-Methoxyindanone (154 mmol) is then added by small portions at −40° C. Stirring continues for 24 hours as the mixture returns to room temperature. After hydrolysis with 300 ml of 1 N HCl, the aqueous phase is extracted 2 times with ethyl acetate. The organic phases are combined, dried on sodium sulfate, concentrated and given form in isopropyl ether to obtain the expected product.
Mass spectrometry (EI): 300 [$M^{+\bullet}$]; 285 [$M-CH_3^\bullet$]$^+$; 269 [$M-OCH_3^\bullet$]$^+$.

Stage B: [2-(3-bromobenzoyl)-4-methoxyphenyl]acetic acid

To a solution of the product of the previous Stage A (153 mmol) in 250 ml of acetone at 0° C. is added a 3.8 M chromium trioxide solution in sulfuric acid (459 mmol). After stirring at 0° C. for 30 minutes, the reaction medium is poured into an ether/ice mixture. The aqueous phase is extracted with ether, then the organic phases are combined, washed with water, dried on sodium sulfate, concentrated and recrystallized in ethyl acetate to obtain the expected compound.
Mass spectrometry (EI): 350 [$M^{+\bullet}$]; 304 [$M^{+\bullet}-CO_2H$]; 225 [305-Br].

Stage C: [2-(3-bromobenzyl)-4-methoxyphenyl]acetic acid

To a solution of the compound of the preceding Stage B (30 mmol) in 50 ml of trifluoroacetic acid cooled in an acetone/ice bath, sodium cyanoborohydride (90 mmol) is added by small fractions. Stirring continues at room temperature for 24 hours. The reaction medium is then poured into an ice/ethyl acetate mixture. 1 N soda solution is added until a pH of around 5 is obtained. The aqueous phase is extracted with ethyl acetate. The organic phases are dried on sodium sulfate, filtered, concentrated and purified on a silica column (eluent: dichloromethane/methanol 99/1) to obtain the expected compound.
Mass spectrometry (EI): 332 [$M^{+\bullet}$].
Mass spectrometry (ESI+): 333 [M+H]$^+$; 355 [M+Na]$^+$.

Stage D: 7-bromo-3-methoxy-5,11-dihydro-10H-dibenzo[a,d]cyclohepten-10-one

To a solution of the compound of the preceding Stage C (32 mmol) in dichloromethane and a few drops of dimethylformamide, a 2 M oxalyl chloride solution in dichloromethane (97 mmol) is added dropwise. The reaction medium is stirred at room temperature for 1 hour, concentrated, dried and then taken up in dichloromethane at 0° C. Aluminum trichloride (65 mmol) is then added by small fractions. After stirring at 0° C. for 30 minutes, the reaction medium is poured into an ice/dichloromethane mixture. The aqueous phase is extracted with dichloromethane. The organic phases are combined, dried on sodium sulfate, filtered and purified on a silica column (eluent: dichloromethane) to obtain the expected compound.
Mass spectrometry (EI): 318 [$M^{+\bullet}$]; 237 [$M^{+\bullet}-Br$].

Stage E: 7-methoxy-11-oxo-10,11-dihydro-5H-dibenzo[a,d]cycloheptene-3-carbonitrile To a solution of the compound of the preceding Stage D (8.5 mmol) in 15 ml of dimethylformamide are added $Zn(CN)_2$ (8.5 mmol) and $Pd(PPh_3)_4$ (0.85 mmol). The reaction medium is stirred at 90° C. for 3 hours and then concentrated and purified on a silica column (eluent: dichloromethane/cyclohexane 70/30) to obtain the expected compound.
Mass spectrometry (EI): 263 [$M^{+\bullet}$]; 232 [$M-OCH_3^\bullet$]$^+$; 204 [232-CO]; 177 [204-HCN].

Stage F: ethyl(7-cyano-3-methoxy-5H-dibenzo[a,d] cyclohepten-10-yl)acetate

A 1 N lithium hexamethyldisilazide solution in THF (140 ml) is added dropwise to 13 ml of ethyl acetate under an argon stream at −78° C. After 15 minutes of stirring, a solution of the compound of the preceding Stage E (22 mmol) in 200 ml of THF is added dropwise. Stirring continues at −78° C. for 45 minutes. The reaction medium is then poured into an ice/ether mixture. The aqueous phase is extracted with ether. The organic phases are combined, dried on sodium sulfate, filtered, concentrated and then dissolved in 50 ml of trifluoroacetic acid. The medium is stirred at room temperature for 1.5 hours and then poured into an ice/ether/$NaHCO_3$ mixture. The aqueous phase is extracted with ether. The organic phases are combined, dried on sodium sulfate, filtered and concentrated to obtain the expected compound.
Mass spectrometry (ESI+): 334 [M+H]$^+$; 356 [M+Na]$^+$.

Stage G: ethyl(3-methoxy-7-{[(trifluoroacetyl) amino]methyl}-5H-dibenzo[a,d]cyclohepten-10-yl) acetate The compound of the preceding Stage F (41 mmol) in 1 l of ethanol, 250 ml of 25% ammonia and 1 g of Raney nickel are pressurized with hydrogen (40-50 psi) for 4 hours. After filtration, the medium is concentrated and the residue is dissolved in 30 ml of dichloromethane, then 30 ml of water is added. The aqueous phase is extracted with dichloromethane. The organic phases are combined, dried on sodium sulfate, filtered and concentrated. The product obtained is treated with a solution of trifluoroacetic anhydride (0.2 mol) and triethylamine (41 mmol) in 40 ml of dichloromethane. The medium is stirred at room temperature for 3 hours, concentrated and taken up in 200 ml of dichloromethane. The organic phase is washed with 200 ml of water, dried on sodium sulfate, filtered, concentrated and purified on a silica column (eluent: cyclohexane/ethyl acetate 70/30) to obtain the expected compound.
Mass spectrometry (EI): 433 [$M^{+\bullet}$]; 360 [$M-C_2H_5CO_2^\bullet$]$^+$; 346 [$M-C_2H_5CO_2CH_2^\bullet$]$^+$.
Mass spectrometry (ESI+): 434 [M+H]$^+$; 456 [M+Na]$^+$; 472 [M+K]$^+$.

Stage H: ethyl(3-methoxy-7-{[(trifluoroacetyl) amino]methyl}-10,11-dihydro-5H-dibenzo[a,d]cyclohepten-10-yl)acetate The compound of the preceding Stage G (25 mmol) and 1 g of Pd(OH)$_2$ in 1 l of ethanol are pressurized with hydrogen (60 psi) for 16 hours, then the solution is filtered and concentrated under vacuum to obtain the expected compound.
Mass spectrometry (EI): 435 [$M^{+\bullet}$]; 389 [$M-HOC_2H_5$]$^{+\bullet}$; 347 [$M-CH_3CO_2C_2H_5$]$^{+\bullet}$.

Stage I: ethyl(3-hydroxy-7-{[(trifluoroacetyl)amino]methyl}-10,11-dihydro-5H-dibenzo[a,d]cyclohepten-10-yl)acetate To a solution of the compound of the preceding Stage H (21.7 mmol) in 100 ml of dichloromethane at 0° C., 67 ml of $BBr_3$ is added. After stirring at 0° C. for 1.75 hours, the reaction medium is poured into an ice/1 M $NaHCO_3$/dichloromethane mixture. The aqueous phase is extracted with dichloromethane. The organic phases are combined, dried on sodium sulfate, filtered, and concentrated to obtain the expected compound.

Mass spectrometry (EI): 421 $[M^{+\bullet}]$; 375 $[M-HOC_2H_5]^+$; 333 $[M-CH_3CO_2C_2H_5]^{+\bullet}$.

Stage J: ethyl(3-{3-[(4-methyl-1-oxydo-2-pyridinyl)amino]propoxy}-7-{[(triflaoroacetyl)amino]methyl}-10,11-dihydro-5H-dibenzo[a,d]cyclohepten-10-yl)acetate To a solution of 2[(3-hydroxypropyl)amino]-4-methylpyridine-N-oxide (42 mmol), $PPH_3$ (42 mmol) and the compound of the preceding Stage I (21 mmol) in 430 ml of dichloromethane at 0° C., diisopropyl azodicarboxylate (42 mmol) is added dropwise. The reaction mixture is stirred at room temperature for 6 hours, concentrated and purified on a silica column (eluent: dichloromethane/methanol 95/5) to obtain the expected compound.

Mass spectrometry (EI): 585 $[M^{+\bullet}]$; 569 $[M-O]^{+\bullet}$; 498 $[M-CH_2CO_2C_2H_5^{\bullet}]^+$.

Mass spectrometry (ESI+): 586 $[M+H]^+$.

Stage K: ethyl(3-{3-[(4-methyl-2-pyridinyl)amino]propoxy}-7-{[(trifluoroacetyl)amino]methyl}-10,11-dihydro-5H-dibenzo[a,d]cyclohepten-10-yl)acetate The compound of the preceding Stage J (18 mmol) and $Pd(OH)_2$ (5.1 g) in 130 ml of isopropanol and 100 ml of cyclohexene are heated under reflux for 12 hours. The crude reaction product is filtered, concentrated and purified on a silica column (eluent: dichloromethane/methanol 97/3) to obtain the expected compound.

Mass spectrometry (ESI+): 570 $[M+H]^+$; 1139 $[2M+H]^+$.

The two enantiomers are separated by preparative chromatography on a 250×50 mm Chiralpak IA 5 µm column (eluent: dichloromethane/heptane/diethylamine 55/45/0.1).

Stage L: (7-(aminomethyl)-3-{3-[(4-methyl-2-pyridinyl)amino]propoxy}-10,11-dihydro-5H-dibenzo[a,d]cyclohepten-10-yl)acetic acid A solution of the compound of the preceding Stage K (7 mmol) in 30 ml of a 2 N soda solution and 75 ml of ethanol is stirred at room temperature for 12 hours. The reaction medium is extracted with diethyl ether and the aqueous phase is brought to pH 8 with HCl solution at 0° C. The precipitate is filtered and dried to obtain the stated product.

Melting point: 226° C.

Optical rotation: $[\alpha_D]^{20°}$=−32° (c=5 mg/ml, $H_2O/CH_3CN$ 1:1).

Mass spectrometry (ESI+): 429 $[M-NH_3+H]^+$; 446 $[M+H]^+$; 468 $[M+Na]^+$; 490 $[M-H+2Na]^+$.

$^1$H NMR analysis (400 MHz, DMSO, δ in ppm): 1.94 (qt, 2H); 2.15 (s, 3H); 2.53-2.63 (dd, 2H); 2.84/3.21 (dd, 2H); 3.36 (q, 2H); 3.68 (m, 1H); 3.90-4.23- (d, 2H); 3.93 (s, 2H); 4.00 (t, 2H); 6.35 (s, 1H); 6.36 (d, 1H); 6.69 (dd, 1H); 6.81 (d, 1H); 6.98 (d, 1H); 7.21 (d, 1H); 7.28 (d, 1H); 7.29 (s, 1H); 7.81 (d, 1H); 8.29 (bs, 3H); 12.24 (bs, 1H).

PREPARATION 2

(7-{[(2-amino-5-{[(11-(carboxymethyl)-7-{3-[(4-methyl-2-pyridinyl)amino]propoxy}-10,11-dihydro-5H-dibenzo[a,d]cyclohepten-3-yl)methyl]amino}-5-oxopentanoyl)amino]methyl}-3-{3-[(4-methyl-2-pyridinyl)amino]propoxy}-10,11-dihydro-5H-dibenzo[a,d]cyclohepten-10-yl)acetic acid A solution of the compound of Preparation 1 (0.387 mmol) and tert-butyl 4-[(2,5-dioxo-1-pyrrolidinyl)oxy]-1-{[(2,5-dioxo-1-pyrrolidinyl)oxy]carbonyl}-4-oxobutylcarbamate [or Boc-Glu(OSu)-OSu] (0.193 mmol) in 3 ml of dimethylformamide is stirred at room temperature for 12 hours. The crude reaction product is purified by preparative chromatography and then the product is taken up in 2 ml of trifluoroacetic acid and stirred at room temperature for 4 hours to yield the stated compound.

Preparative Chromatography Conditions:
Symmetry C18 7 µm column;
Eluent A: water/0.1% TFA;
Eluent B: acetonitrile/0.1% TFA;
Gradient of 25% to 90% of B in 30 minutes at 70 ml/min;
Retention time=23.77 minutes.

$^1$H NMR analysis (400 MHz, DMSO, δ in ppm): 1.98 (m, 6H); 2.25 (s, 6H); 2.27 (m, 2H); 2.45 (dd, 2H); 2.57 (dd, 2H); 2.81 (m, 2H); 3.19 (m, 2H); 3.40 (m, 4H); 3.63 (m, 2H); 3.81 (m, 1H); 3.85 (dd, 2H); 4.00 (t, 4H); 4.20 (m, 5H); 4.31 (dd, 1H); 6.62 (bd, 2H); 6.69 (m, 4H); 6.79 (d, 2H); 6.97 (dd, 2H); 7.00-7.15 (m, 6H); 7.80 (d, 2H); 8.17 (vbs, 3H); 8.42 (t, 1H); 8.84 (bt, 1H); 12.25 (bs, 2H).

EXAMPLE 1

Fluorescein Conjugate of the Compound of Preparation 1

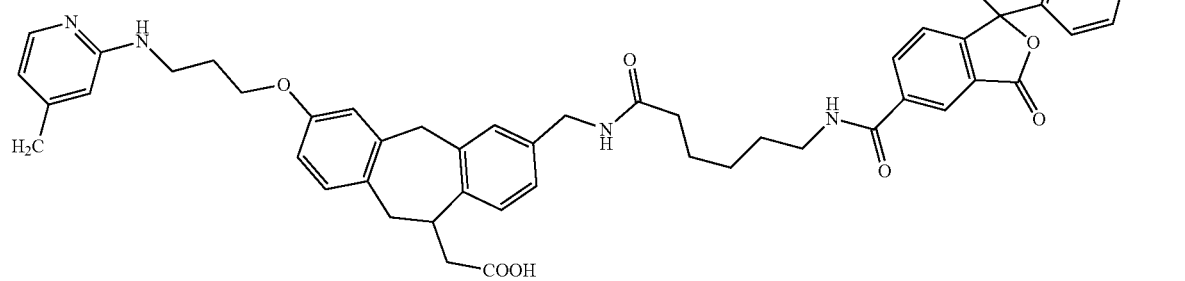

A solution of the compound of Preparation 1 (35 µmol) and fluorescein-5(6)-carboxamidocaproic acid N-hydroxysuccinimide ester (43.5 µmol) in 5 ml of THF and 2 ml of dimethylformamide is stirred at room temperature for 12 hours. The crude reaction product is purified by preparative chromatography to obtain the stated compound.

Preparative Chromatography Conditions:
Chromasil C18 5 µm column;
Eluent A: water/0.1% TFA;
Eluent B: acetonitrile/0.1% TFA;
Gradient from 20% to 100% of B in 30 minutes at 1 ml/min;
Retention time=15.14 minutes.

$^1$H NMR analysis (400 MHz, DMSO, δ in ppm): 1.24-1.34 (qt, 2H); 1.49 (m, 2H); 1.58 (qt, 2H); 2.01 (bqt, 2H); 2.09-2.15 (t, 2H); 2.30 (s, 3H); 2.45 (m, 1H); 2.58 (m, 1H); 2.83 (dd, 1H); 3.19 (m, 1H); 3.19-3.31 (q, 2H); 3.45 (bq, 2H); 3.62 (m, 1H); 3.86 (dd, 1H); 4.03 (m, 2H); 4.16 (m, 3H); 6.57 (m, 4H); 6.70 (m, 4H); 6.81 (m, 2H); 6.95-7.15 (m, 4H); 7.36-8.07 (d, 1H); 7.67-8.46 (s, 1H); 7.79 (d, 1H); 8.15-8.25 (m, 2H); 8.51 (bs, 1H); 8.65-8.79 (bt, 1H); 10.14 (bs, 2H); 12.20 (bs, 1H); 12.95 (bs, 1H).

Retention time=4.51 minutes.

Mass spectrometry (ESI+): 529.8 [M+2H]$^{2+}$; 1058.6 [M+H]$^+$.

$^1$H NMR analysis (600 MHz, DMSO, δ in ppm): 1.30 (t, 3H); 1.38 (qt, 2H); 1.59 (qt, 2H); 1.69 (s, 12H); 1.73 (m, 2H); 1.96 (qt, 2H); 2.12 (t, 2H); 2.29 (s, 3H); 2.45 (dd, 1H); 2.57 (dd, 1H); 2.79 (dd, 1H); 3.17 (dd, 1H); 3.41 (q, 2H); 3.61 (m, 1H); 3.84 (d, 1H); 3.97 (t, 2H); 4.10 (t, 2H); 4.13 (m, 2H); 4.14 (d, 2H); 4.17 (d, 1H); 6.50 (d, 1H); 6.52 (d, 1H); 6.65 (dd, 1H); 6.71 (d, 1H); 6.78 (d, 1H); 6.85 (bs, 1H); 6.95 (d, 1H); 7.00 (dd, 1H); 7.02 (d, 1H); 7.08 (d, 1H); 7.39 (d, 1H); 7.69 (m, 2H); 7.80 (dl, 1H); 7.82 (bs, 2H); 8.23 (t, 1H); 8.34 (t, 1H); 8.59 (bs, 1H); 12.25 (bs, 1H); 12.91 (bs, 1H).

EXAMPLE 2

Cy™ 3 Conjugate of the Compound of Preparation 1

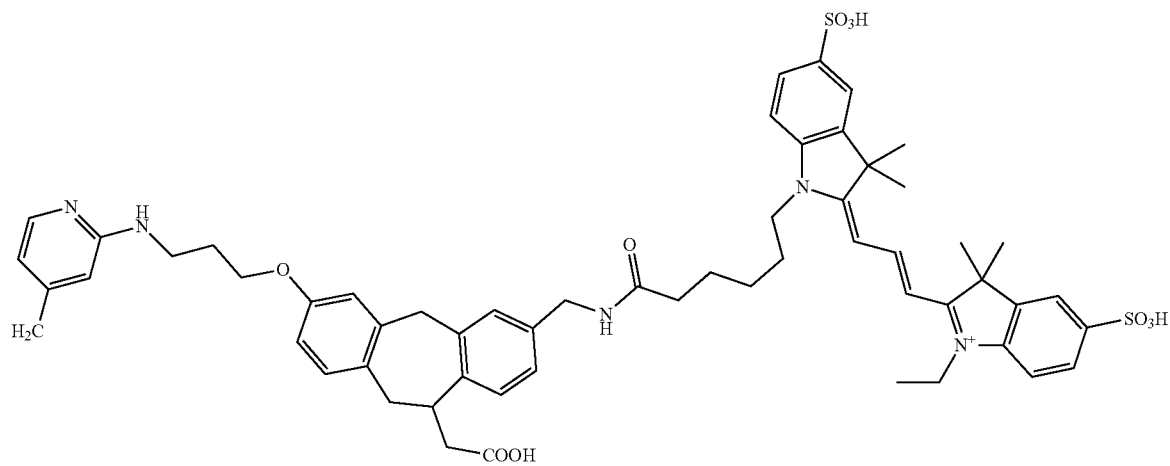 [SMILES: CC[N+]1=C(/C=C/C=C2/N(CCCCCC(=O)NCc3ccc4c(c3)Cc3cc(OCCCNc5cc(C)ccn5)ccc3CC4CC(=O)O)c3ccc(S(=O)(=O)O)cc3C2(C)C)C(C)(C)c2cc(S(=O)(=O)O)ccc21]

A solution of the compound of Preparation 1 (13.5 µmol), Cyanin3 MonoNHS ester (item PA13102 GE Healthcare) (13 µmol) and 100 µl of triethylamine in 2 ml of DMSO is stirred at room temperature for 12 hours. The crude reaction product is purified by preparative chromatography to yield the expected compound.

Preparative Chromatography Conditions:
XTerra MS C18 2.5 µm column;
Eluent A: water/acetonitrile/methanesulfonic acid 1000/25/1;
Eluent B: acetonitrile/water/methanesulfonic acid 1000/25/1;
Gradient from 0 to 100% of B in 10 minutes at 0.81 ml/min;

EXAMPLE 3

Cy™ 5.5 Conjugate of the Compound of Preparation 1

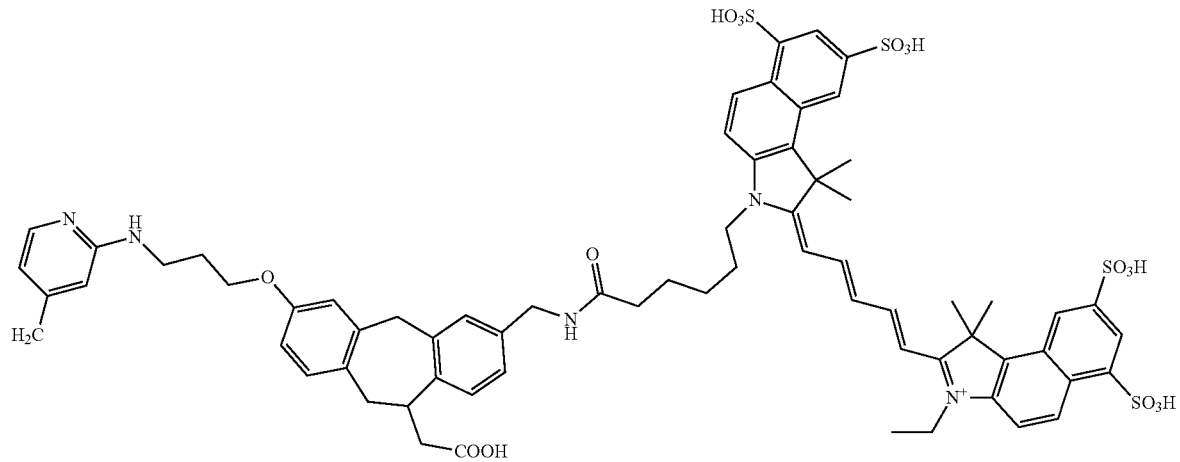

A solution of the compound of Preparation 1 (9 µmol), of Cyanin5.5 MonoNHS ester (item PA15602 GE Healthcare) (8.86 µmol) and 150 µl of triethylamine in 2 ml of DMSO is stirred at room temperature for 12 hours. The crude reaction product is purified by preparative chromatography to obtain the expected compound.

Preparative Chromatography Conditions:
 XTerra MS C18 2.5 µm column;
 Eluent A: water/acetonitrile/methanesulfonic acid 1000/25/1;
 Eluent B: acetonitrile/water/methanesulfonic acid 1000/25/1;
 Gradient from 0 to 100% of B in 10 minutes at 0.81 ml/min;
 Retention time=4.67 minutes.

Mass spectrometry (ESI+): 672.8 $[M+2H]^{2+}$; 683.8 $[M+H+Na]^{2+}$; 1344.6 $[M+H]^+$.

$^1$H NMR analysis (600 MHz, DMSO, δ in ppm): 1.33 (t, 3H); 1.37 (qt, 2H); 1.58 (qt, 2H); 1.77 (qt, 2H); 1.90 (qt, 2H); 1.92 (s, 6H); 1.95 (2s, 6H); 2.09 (t, 2H); 2.27 (s, 3H); 2.43 (dd, 1H); 2.55 (dd, 1H); 2.75 (dd, 1H); 3.12 (dd, 1H); 3.37 (q, 2H); 3.81 (d, 1H); 3.90 (t, 2H); 4.08 (m, 2H); 4.13 (d, 1H); 4.22 (pt, 2H); 4.26 (ql, 2H); 6.34 (d, 2H); 6.57 (dd, 1H); 6.61 (t, 1H); 6.68 (dd, 1H); 6.74 (d, 1H); 6.83 (bs, 1H); 6.88 (d, 1H); 6.97 (dd, 2H); 7.04 (m, 1H); 7.74 (2d, 2H); 7.78 (m, 1H); 8.17 (t, 1H); 8.20 (d, 1H); 8.22 (d, 1H); 8.43 (m, 2H); 8.44 (s, 1H); 8.46 (s, 1H); 8.56 (vbs, 1H); 9.02 (d, 2H); 12.90 (bs, 1H).

EXAMPLE 4

Cy™ 7 Conjugate of the Compound of Preparation 1

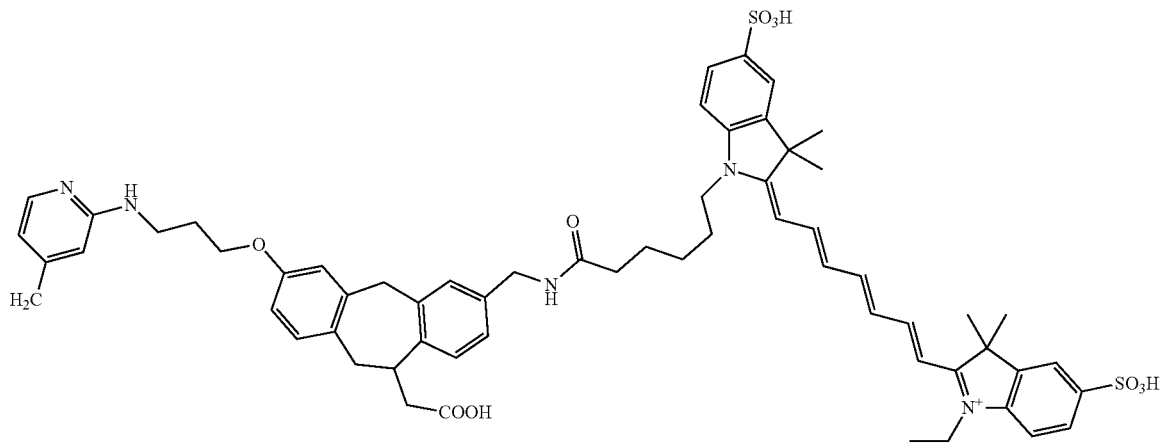 [SMILES: CC[N+]1=C(/C=C/C=C/C=C/C=C2/N(CCCCCC(=O)NCc3ccc4c(c3)Cc3cc(OCCCNc5cc(C)ccn5)ccc3CC4CC(=O)O)c3ccc(S(=O)(=O)O)cc3C2(C)C)C(C)(C)c2cc(S(=O)(=O)O)ccc21]

A solution of the compound of Preparation 1 (13.5 µmol), Cyanin7 MonoNHS ester (item PA17102 GE Healthcare) (12.2 µmol) and 100 µl of triethylamine in 2 ml of DMSO is stirred at room temperature for 2 hours. The crude reaction product is purified by preparative chromatography to obtain the expected compound.

Preparative Chromatography Conditions:
 XTerra MS C18 2.5 µm column;
 Eluent A: water/acetonitrile/methanesulfonic acid 1000/25/1;
 Eluent B: acetonitrile/water/methanesulfonic acid 1000/25/1;
 Gradient from 0 to 100% of B in 10 minutes at 0.81 ml/min;
 Retention time=4.95 minutes.

Mass spectrometry (ESI+): 555.8 [M+2H]$^{2+}$; 566.8 [M+H+Na]$^{2+}$; 574.8 [M+H+K]$^{2+}$; 1110.7 [M+H]$^{+}$.

$^{1}$H NMR analysis (600 MHz, DMSO, δ in ppm): 1.26 (t, 3H); 1.34 (qt, 2H); 1.57 (qt, 2H); 1.61 (s, 6H); 1.63 (s, 6H); 1.68 (qt, 2H); 1.95 (qt, 2H); 2.11 (t, 2H); 2.30 (s, 3H); 2.45 (dd, 1H); 2.57 (dd, 1H); 2.80 (dd, 1H); 3.17 (dd, 1H); 3.41 (q, 2H); 3.61 (m, 1H); 3.85 (d, 1H); 3.97 (t, 2H); 4.03 (bt, 2H); 4.12 (bt, 2H); 4.14 (d, 2H); 4.18 (d, 1H); 6.33 (d, 1H); 6.39 (d, 1H); 6.53 (m, 2H); 6.65 (dd, 1H); 6.71 (d, 1H); 6.79 (d, 1H); 6.84 (bs, 1H); 6.95 (d, 1H); 7.01 (d, 1H); 7.03 (s, 1H); 7.09 (d, 1H); 7.27 (d, 1H); 7.32 (d, 1H); 7.63 (dd, 1H); 7.64 (dd, 1H); 7.72-7.79 (m, 3H); 7.80 (d, 1H); 7.85 (t, 1H); 7.90 (t, 1H); 8.21 (t, 1H); 8.30-8.80 (vbs, 2H); 12.25 (bs, 1H); 12.92 (bs, 1H).

A solution of the compound of Preparation 1 (24.4 μmol) and 1-[(3-iodobenzoyl)oxy]pyrrolidine-2,5-dione (24.4 μmol) in triethylamine dried on potassium carbonate (11 mg) is stirred at room temperature for 1 hour. The crude reaction product is purified on a silica column (eluent: dichloromethane/methanol 99/1) to obtain the expected compound.

Mass spectrometry (ESI+): 676.2 [M+H]$^{+}$; 1351.4 [2M+H]$^{+}$.

$^{1}$H NMR analysis (400 MHz, DMSO, δ in ppm): 2.00 (qt, 2H); 2.28 (s, 3H); 2.46 (dd, 1H); 2.58 (dd, 1H); 2.83 (dd, 1H); 3.19 (dd, 1H); 3.43 (q, 2H); 3.63 (m, 1H); 3.87 (d, 1H); 4.02 (t, 2H); 4.19 (d, 1H); 4.39 (d, 2H); 6.65 (m, 1H); 6.68 (dd, 1H); 6.76 (m, 1H); 6.81 (d, 1H); 6.98 (d, 1H); 7.11 (m, 3H); 7.28 (t, 1H); 7.78 (d, 1H); 7.89 (m, 2H); 8.23 (t, 1H); 8.0-8.5 (bs, 1H); 9.04 (t, 1H); 12.19 (bs, 1H); 12.87 (bs, 1H).

EXAMPLE 5

Alexa Fluor® 750 Conjugate of the Compound of Preparation 1

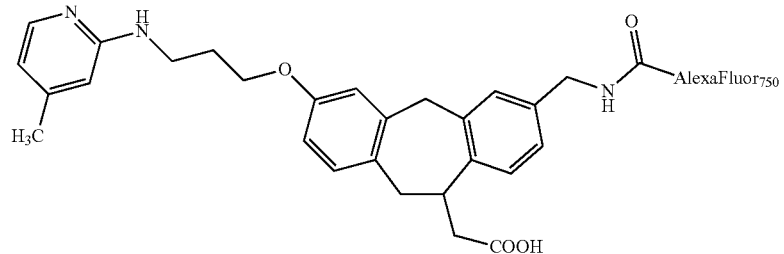

A solution of the compound of Preparation 1 (4.4 μmol), Alexa Fluor® 750 succinimidyl ester (1.54 μmol) dissolved in 200 μl of dry dimethylformamide and triethylamine dried on potassium carbonate (7.2 μmol) is stirred at room temperature for 1 hour. The crude reaction product is purified by preparative chromatography to obtain the expected compound.

Preparative Chromatography Conditions:
Prochrom LC50 Symmetry C18 7 μm column;
Eluent A: water+0.2% trifluoroacetic acid;
Eluent B: acetonitrile+0.2% trifluoroacetic acid;
Gradient from 5% to 55% of B in 30 minutes at 70 ml/min;
Retention time=15.8 minutes.

EXAMPLE 6

[$^{125}$I] (7-{[(3-iodobenzoyl)amino]methyl}-3-{3-[(4-methyl-2-pyridinyl)amino]propoxy}-10,11-dihydro-5H-dibenzo[a,d]cyclohepten-10-yl)acetic acid

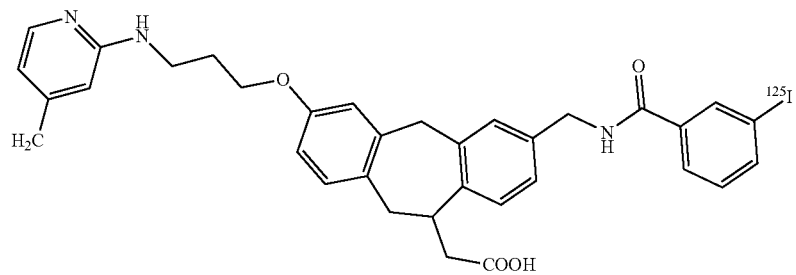 [SMILES: Cc1ccnc(NCCCOc2ccc3c(c2)Cc2cc(CNC(=O)c4cccc([125I])c4)ccc2C(CC(=O)O)C3)c1]

EXAMPLE 7

(7-({[(6-hydrazino-3-pyridinyl)carbonyl]amino}methyl)-3-{3-[(4-methyl-2-pyridinyl)amino]propoxy}-10,11-dihydro-5H-dibenzo[a,d]cyclohepten-10-yl)acetic acid

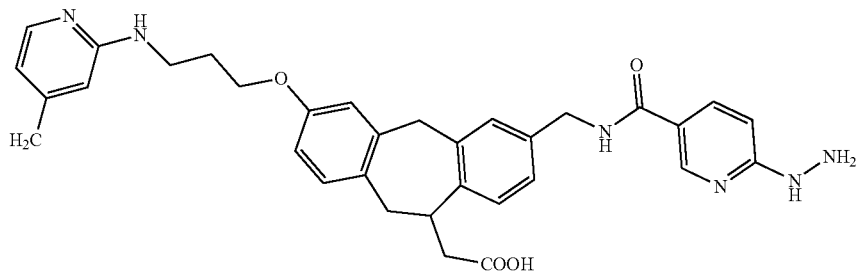 [SMILES: Cc1ccnc(NCCCOc2ccc3c(c2)Cc2cc(CNC(=O)c4ccc(NN)nc4)ccc2C(CC(=O)O)C3)c1]

A solution of the compound of Preparation 1 (1 mmol), tert-butyl 2-(5-{[(2,5-dioxopyrrolidin-1-yl)oxy]carbonyl}pyridin-2-yl)hydrazinecarboxylate (1 mmol) and triethylamine (0.1 mmol) in 15 ml of dimethylformamide is stirred at room temperature for 16 hours. The crude reaction product is triturated with 15 ml of ethyl ether and filtered. The residue obtained is treated with 100 ml of a trifluoroacetic acid/dichloromethane 1/1 mixture and purified by preparative chromatography to obtain the expected compound.

Preparative Chromatography Conditions:
 Prochrom LC50 Symmetry C18 7 μm column;
 Eluent A: water+0.2% trifluoroacetic acid;
 Eluent B: acetonitrile+0.2% trifluoroacetic acid;
 Gradient from 5% to 100% of B in 30 minutes at 70 ml/min;
 Retention time=20.7 minutes.

$^1$H NMR analysis (400 MHz, DMSO, δ in ppm): 2.00 (qt, 2H); 2.30 (s, 3H); 2.46 (dd, 1H); 2.56 (dd, 1H); 2.82 (dd, 1H); 3.19 (dd, 1H); 3.45 (m, 2H); 3.63 (m, 1H); 3.87 (d, 1H); 4.02 (t, 2H); 4.19 (d, 1H); 4.39 (d, 2H); 6.69 (dd, 1H); 6.70 (dd, 1H); 6.81 (m, 2H); 6.89 (d, 1H); 6.98 (d, 1H); 7.11 (m, 3H); 7.79 (d, 1H); 8.15 (dd, 1H); 8.49 (bs, 1H); 8.63 (d, 1H); 9.00 (t, 1H); 9.73 (bs, 1H); 12.24 (bs, 1H).

EXAMPLE 8

Alexa Fluor® 750 Conjugate of the Compound of Preparation 2

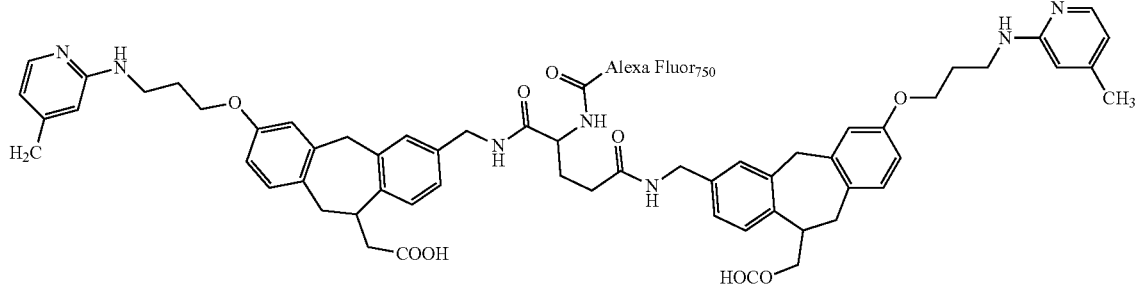

A solution of the compound of Preparation 2 (1.86 μmol), Alexa Fluor® 750 succinimidyl ester (1.54 μmol) dissolved in 200 ml of dry dimethylformamide and triethylamine dried on potassium carbonate (9.4 μmol) is stirred at room temperature for 1 hour. The crude reaction product is purified by preparative chromatography to obtain the expected compound.

Preparative Chromatography Conditions:
 Prochrom LC50 Symmetry C18 7 μm column;
 Eluent A: water+0.2% trifluoroacetic acid;
 Eluent B: acetonitrile+0.2% trifluoroacetic acid;
 Gradient from 5% to 55% of B in 30 minutes at 70 ml/min;
 Retention time=19.7 minutes.

EXAMPLE 9

Conjugate Between a Quantum Dot and the Compound of Preparation 1

A solution of the compound of Preparation 1 (12.8 μmol), 1-ethyl-3-(3-dimethylaminopropyl)carbodiimide hydrochloride (100 mg) in 10 ml of phosphate-buffered saline (pH 7.4) (52 μmol/μl) and the quantum dot T2-MPEviTag™ functionalized by a carboxyl group (E2161CB20680; Evident Technologies) (1.6 nmol) in 100 μl of DMSO is stirred at room temperature for 2.5 hours.

The reaction medium is concentrated to a volume of about 400 μl by centrifuging in a VIVASPIN 2 (100,000 MWCO PES; Vivascience) at 6000 rpm for 5-10 minutes. The residue is then washed 2 times with about 1 ml of Milli-Q water and then purified by exclusion chromatography on 12 ml of Superdex 200 (particle diameter: 24-44 μm) to obtain a solution of the expected compound.

Pharmacological Study

EXAMPLE A

Plasma Pharmacokinetics

In female Swiss nude mice (N=18), the compound of Example 3 solubilized to 10 nmol/ml in 0.9% NaCl solution is injected intravenously (200 μl) into the caudal vein. Blood is collected at various times (5 and 30 minutes then 2, 4, 8 and 24 hours; 3 mice/sample time) and, after centrifugation, the supernatant plasma is transferred to heparinized tubes. The sample is then diluted in 50 μl of a 20 mM ammonium formate/acetonitrile/formic acid 50/50/0.1 buffer mixture to be analyzed by UPLC-MS/MS, ESI+.

After intravenous administration in the mouse, the pharmacokinetics of the compound of Example 3 is characterized by rapid distribution followed by slow elimination with a moderate distribution volume (1 l/mg), a long half-life (15 hours) and a low plasma clearance rate (0.8 ml/min/kg) (FIG. 1).

EXAMPLE B

Targeting of Heterotopically-Transplanted Tumors

In the right rear paw of Swiss nude mice (N=12), 1 to $2 \times 10^6$ tumor cells are inoculated subcutaneously, forming a group of 3 mice for each tumor cell line (A549 human lung adenocarcinoma model; H460 human lung carcinoma model; HCT116 human colorectal carcinoma model; U87MG human glioblastoma model).

When the tumors reach a volume of between 0.5 and 1 cm, the compound of Example 3 (200 μl) solubilized at 10 nmol/ml in phosphate buffer solution (PBS) is injected intravenously.

Under gas anesthesia, 5 acquisitions are carried out at various times of the experiment (2, 4, 6, 8 and 24 hours) using a Caliper IVIS Lumina II apparatus (ex=680 nm; em=720 nm). In parallel, blood samples are taken.

Figure 2:
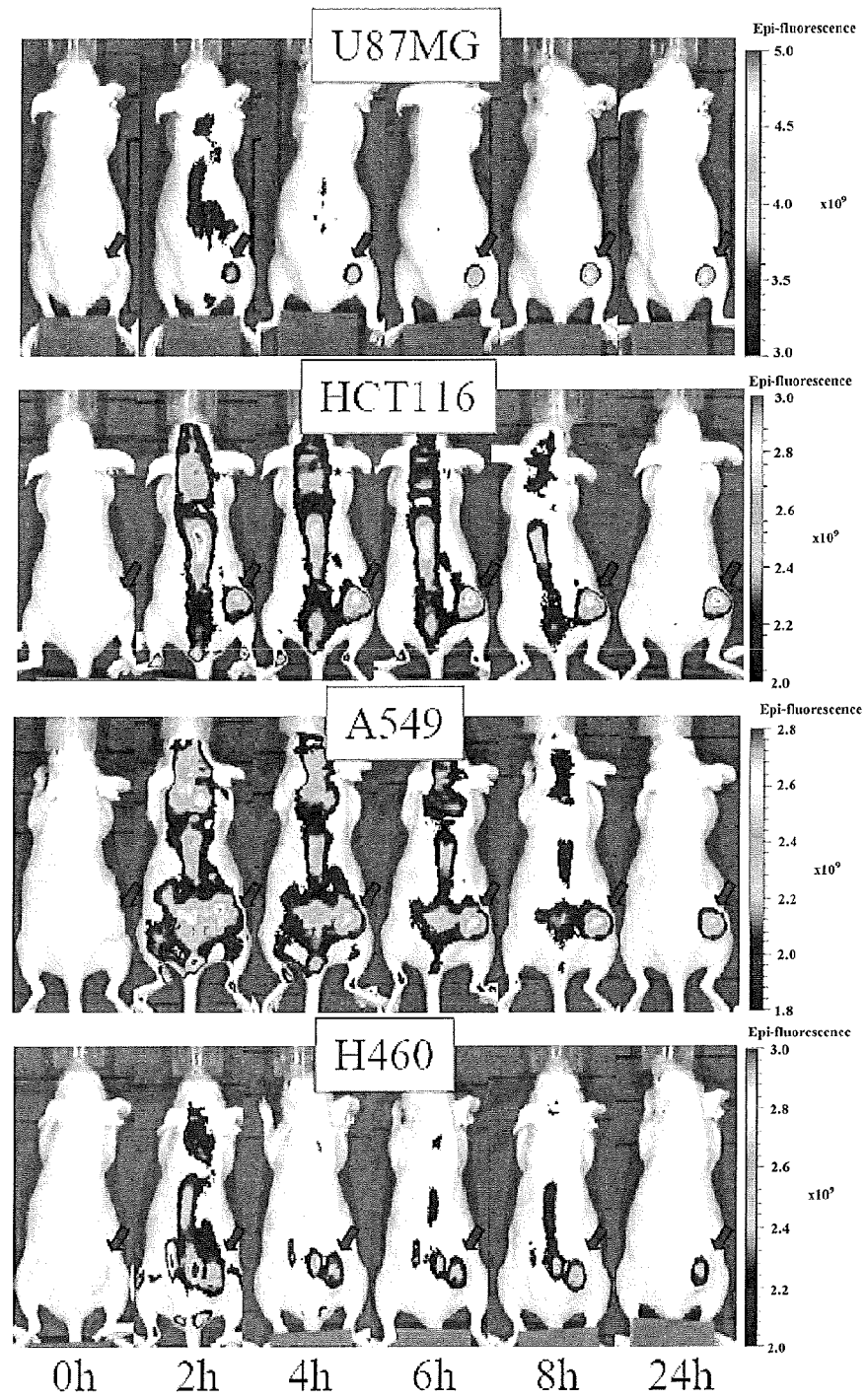
FIG. 2: IR fluorescence imaging of the compound of Example 3 at 2, 4, 6, 8 and 24 hours post-injection in U87MG (glioblastoma), HCT116 (colorectal carcinoma), A549 (pulmonary adenocarcinoma) and H460 (lung carcinoma) tumor xenotransplantation models.
Figure 3:
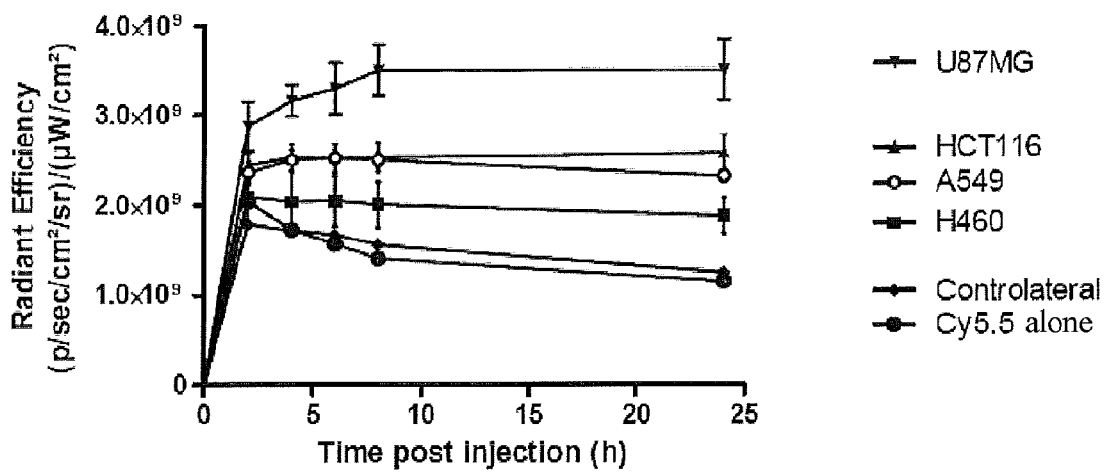
FIG. 3: In vivo kinetics of the fluorescence emitted by the compound of Example 3 and by Cyanine 5.5 alone within the various tumor models and the contralateral area.
Figure 4:
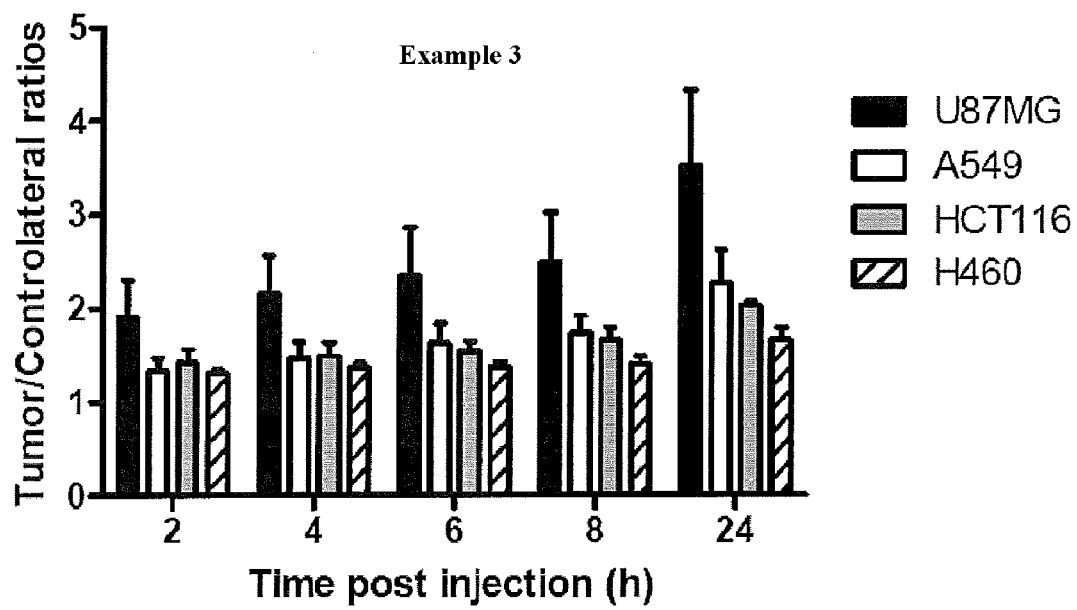
FIG. 4: Ratio of fluorescence between the tumor and the contralateral zone for all cancer cell lines used.

After the animals are euthanized by cervical dislocation, the organs (kidney, liver, spleen, lung, tumor, blood, muscle, heart, intestine) are taken and ex vivo acquisition is carried out (Lumina II: ex=680 nm; em=720 nm).
Fluorescence Imaging of the Compound of Example 3 In Vivo at 2 nmol As shown in FIG. 2, whatever cancer line is used, the tumors targeted by the compound of Example 3 are clearly visible 24 hours post-injection.
Kinetics of the Compound of Example 3 In Vivo The kinetics show maximum tumor fixation between 6 and 8 hours post-injection and then they remain stable up to 24 hours for each cancer cell line (FIG. 3). However, the best contrast is observed for the later times when the slow elimination kinetics of the free tracer allows obtaining minimal background noise in healthy tissues.
Tumor Tissue/Healthy Tissue Ratio According to the tumor cell line observed, A549, H460, HCT116 or U87MG, the tumor/healthy tissue ratios at $t_{24h}$ are respectively 2.3, 1.66, 2 and 3.5 (FIG. 4). The contrast increases progressively over time due to the slow elimination of the probe in the plasma compartment.

Biodistribution in the Major Organs and Tissues

Figure 5A:
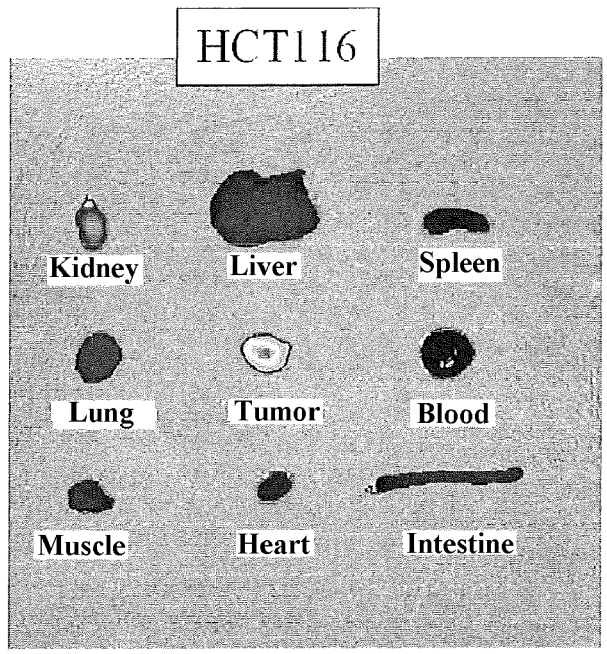
FIG. 5: Ex vivo imaging of IR fluorescence at $t_{24h}$ of the compound of Example 3 in the various organs, tissues and tumors (A: HCT116; B: H460; C: A549).
Figure 5B:
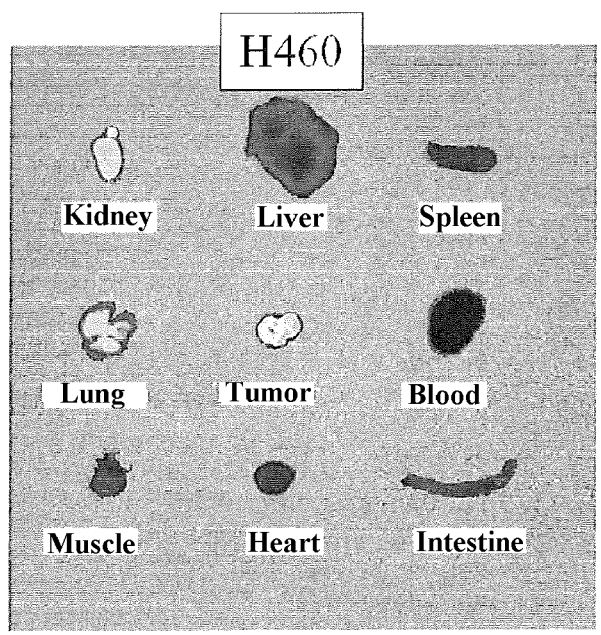
Figure 5C:
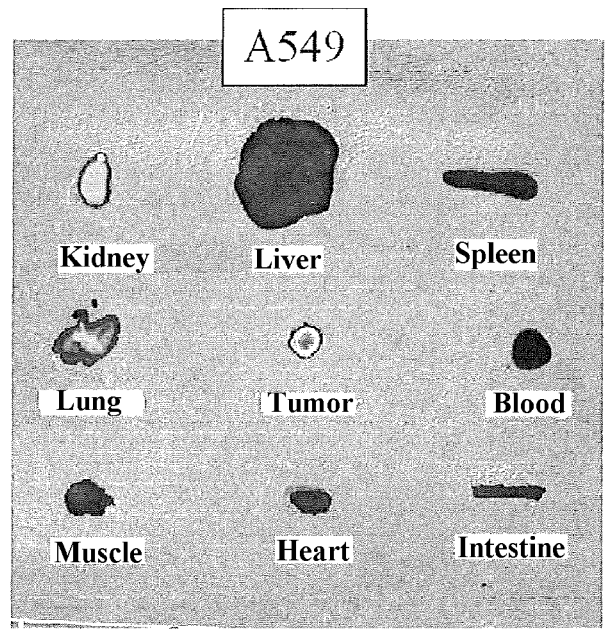

The study of the biodistribution of the compound of Example 3, in the principal organs, 24 hours after injection, shows a high specificity of the probe for the tumor with a limited concentration in the most voluminous organs, which is particularly favorable to imaging in vivo. For example, the tumor volume emits on average 12 times more signal than muscle tissue (FIGS. 5A, 5B and 5C).

Figure 6:
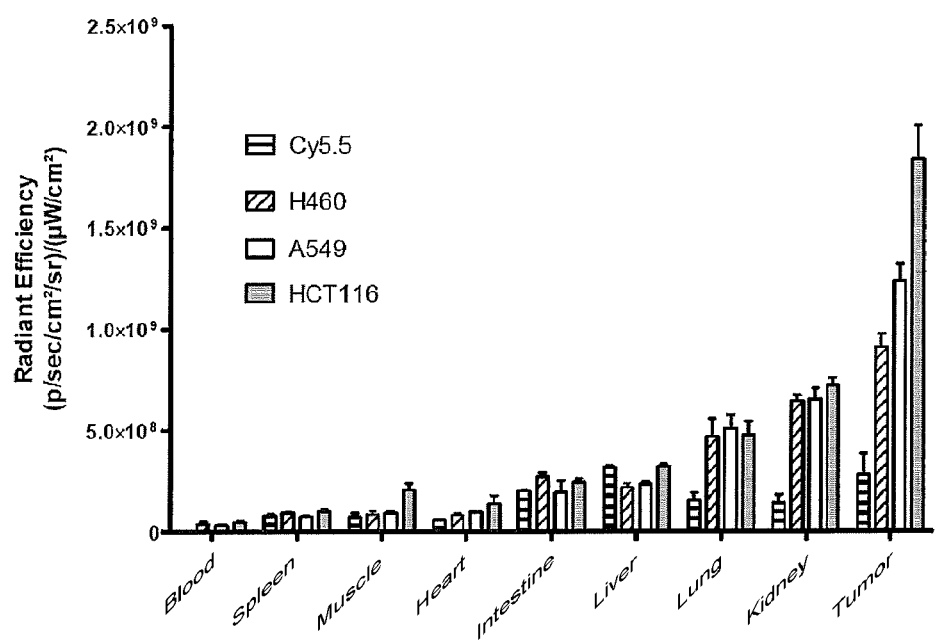
FIG. 6: Ex vivo quantification at $t_{24h}$ of the biodistribution of the compound of Example 3 in the various organs, tissues and tumors.
Figure 7:
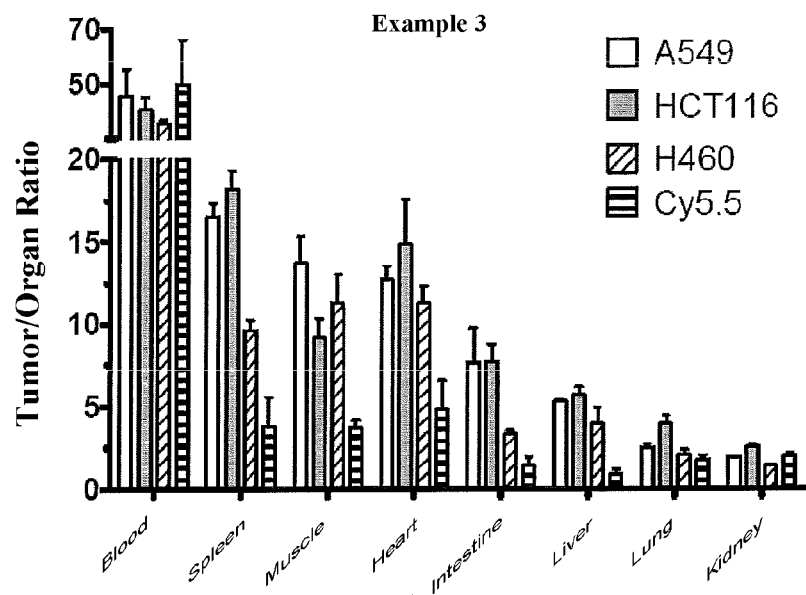
FIG. 7: Evaluation of the Tumor/Organ ratio at $t_{24h}$ of the compound of Example 3 in the organs, tissues and tumors.

Elimination of this type of probe is principally renal with intrinsic fixation in the kidney (FIG. 6). Furthermore, the compound of Example 3 has weak renal fixation (tumor/kidney ratio=2), a particularly advantageous property for imaging abdominal areas (FIG. 7).

EXAMPLE C

Targeting of Spontaneous Tumors

On the K-rasLA1 murine model spontaneously developing bronchioloalveolar carcinoma, tumor development is controlled by X-ray scanner synchronized on respiration before injection of the product to be tested. The compound of Example 3 (200 μl) solubilized at 10 nmol/ml in phosphate buffer solution (PBS) is then injected intravenously.

After the animals are euthanized, the lungs are taken to be fixed by tracheal injection of neutral formalin. Acquisition of fluorescence ex vivo is carried out using a Caliper IVIS Lumina II apparatus (ex=680 nm; em=720 nm). A photograph of the excised lung is also taken.

Figure 8:
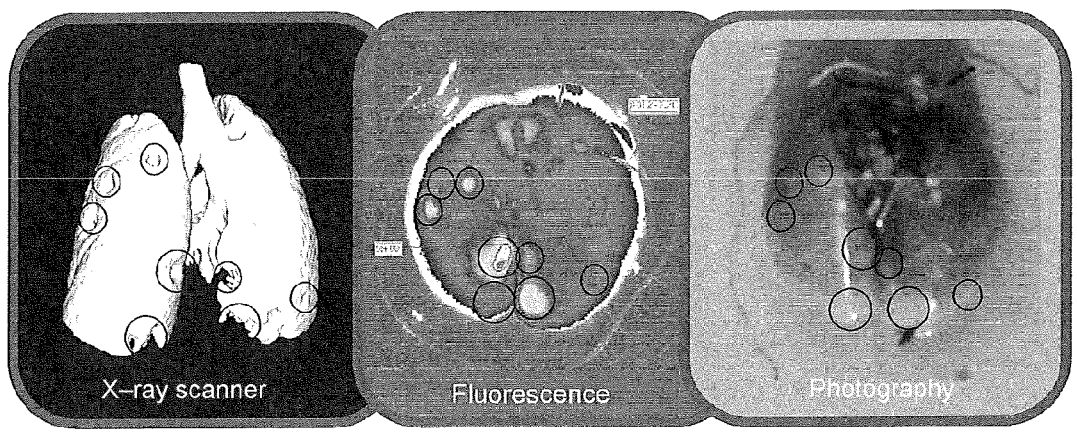
FIG. 8: Multimodal colocalization of spontaneous tumor lesions in the K-rasLA1 murine model.

The results show that the compound of Example 3 confirms its strong potential of targeting with respect to neoplastic lesions formed in situ (FIG. 8) and also known to express integrins.

EXAMPLE D

Interaction with Tumor Development

In the right rear paw of Swiss nude mice (N=12), $3 \times 10^6$ U87MG (human glioblastoma) tumor cells are inoculated subcutaneously. When the tumor reaches a volume of 0.5 cm, luciferin (2 mg/mouse) is injected intraperitoneally in order to carry out bioluminescence acquisition and quantification at D0.

The animals are divided into 3 groups of 4 to form a control group with no injection; a group receiving a single intravenous injection of the compound of Example 3 (2 nmol in 200 μl); and a group receiving a weekly intravenous injection for 4 weeks of the compound of Example 3 (2 nmol in 200 μl). Lastly, bioluminescence acquisition and quantification are carried out 3 times per week after the intraperitoneal injection of luciferin.

Figure 9:
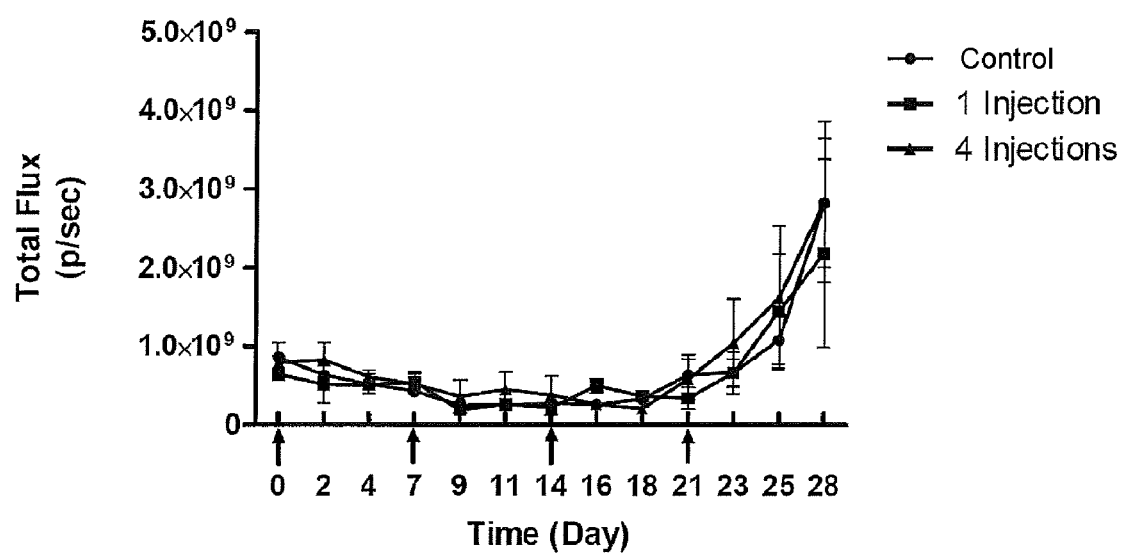
FIG. 9: Kinetics of tumor growth by bioluminescence with or without injection of the compound of Example 3 in Swiss nude mice.

The results show that tumor growth is identical for the three groups (FIG. 9). No anti- or pro-angiogenic effect is observed whether a single injection is carried out or multiple injections are carried out at the concentrations under consideration for imaging in vivo (2 nmol/mouse). Consequently, the compounds of the invention, at the standard doses for imaging, are an excellent, reliable diagnostic tool with no interaction with tumor development.

The invention claimed is:

1. A compound of formula (I):

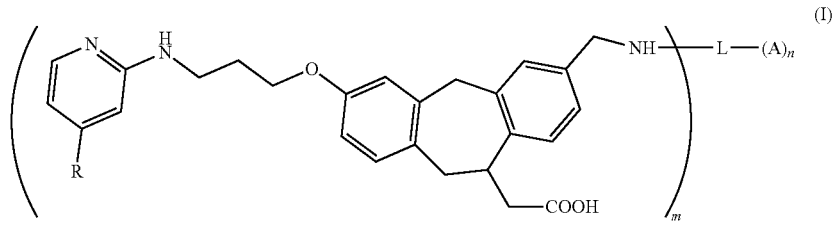

wherein:
R is a linear or branched ($C_1$-$C_6$) alkyl group;
L is a spacer group;
A is a diagnostic agent;
m and n are each independently equal to 1 or 2;
or an enantiomer thereof, a diastereoisomer thereof, or a pharmaceutically acceptable acid or base addition salt thereof.

2. The compound of formula (I) according to claim 1, wherein R is a methyl group.

3. The compound of formula (I) according to claim 1, wherein L is a $C_1$-$C_{20}$ saturated or unsaturated, linear or branched hydrocarbon chain, wherein:
one or more methylene groups can be replaced by an oxygen atom; a —NH— group; a —CO— group; a hydroxy group; a phenyl group; or a pyridine group; and
said hydrocarbon chain forms a —NH—CO— peptide bond with the primary amine of the targeting ligand.

4. The compound of formula (I) according to claim 1, wherein L is a —CO— group; a ($C_1$-$C_6$) alkylcarbonyl group; a phenylcarbonyl group; or a pyridylcarbonyl group.

5. The compound of formula (I) according to claim 1, wherein L is a —CO—($CH_2$)$_5$—NH— group; a

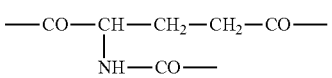

group; or a

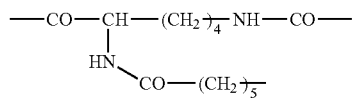

group.

6. The compound of formula (I) according to claim 1, wherein L is a n-pentylcarbonyl group.

7. The compound of formula (I) according to claim 1, wherein A is a fluorophore.

8. The compound of formula (I) according to claim 1, wherein A is fluorescein, Alexa Fluor® 750, Cy™ 3, Cy™ 5.5 or Cy™ 7.

9. The compound of formula (I) according to claim 1, wherein A is Cy™ 5.5.

10. The compound of formula (I) according to claim 1, wherein m and n are equal to 1.

11. The compound of formula (I) according to claim 1, wherein m is equal to 1 and n is equal to 2.

12. The compound of formula (I) according to claim 1, chosen among the following formulas:

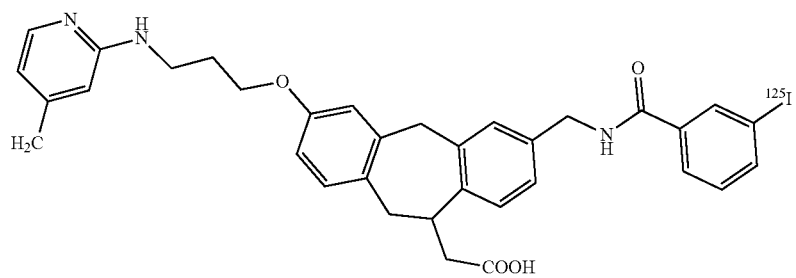

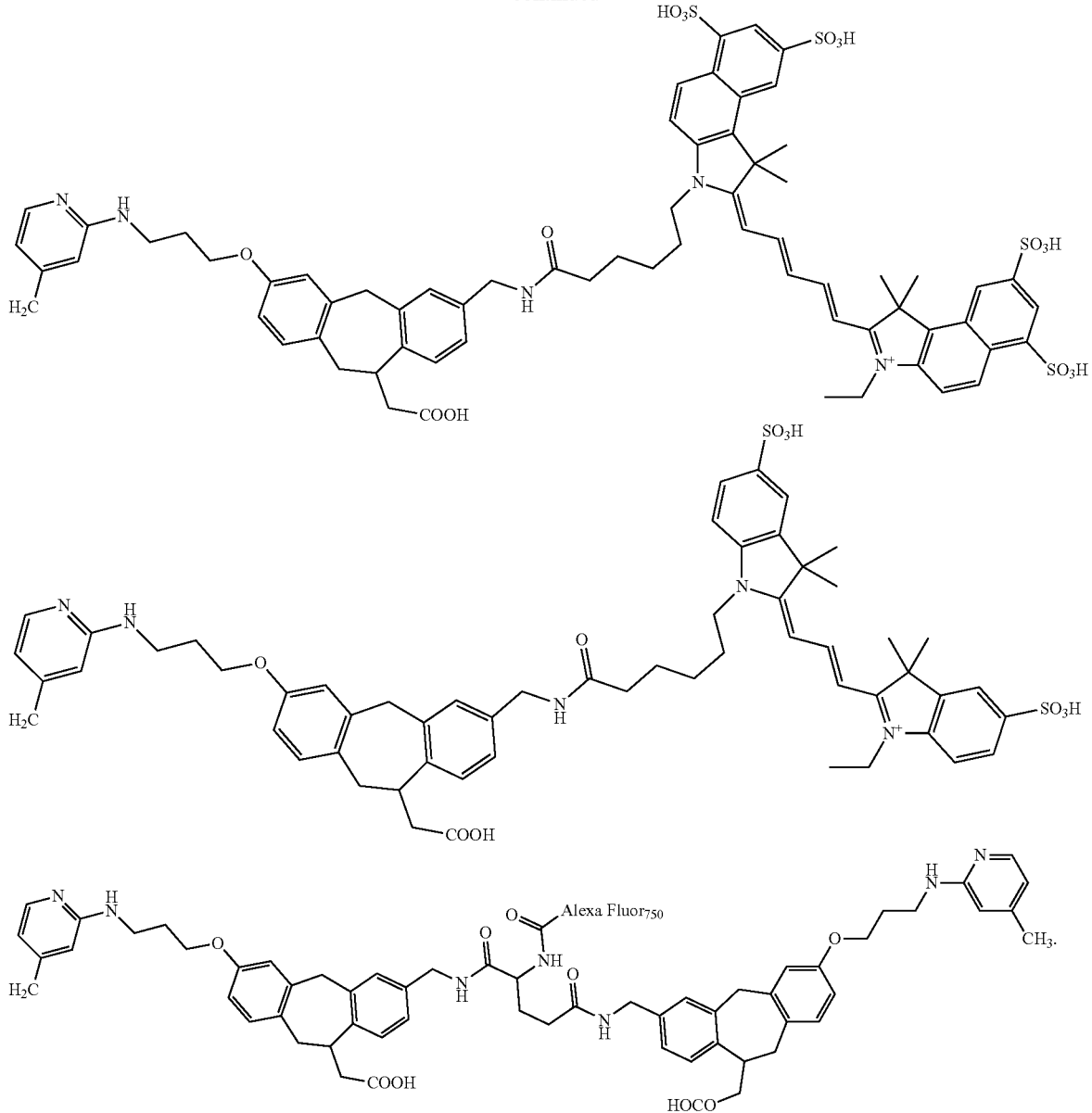

-continued

13. A pharmaceutical composition containing as active ingredient a compound according to claim 1, in combination with one or more inert, nontoxic and pharmaceutically acceptable carriers.

14. A method of imaging or in vivo diagnosis which comprises administering to a patient a pharmaceutical composition according to claim 13 and detecting the location of said composition in said patient.

15. A method of evaluation of the effects of the administration of a drug to an animal or human suffering from a pathology during which neovascularization occurs which comprises successively
 a) administering a pharmaceutical composition according to claim 13 to said patient and detecting the location of said composition;
 b) administering said drug to said patient;
 c) administering said composition to said patient again and detecting the location of said composition; and
 d) comparing the location of the said composition in step a) with the location of said composition in step c).

16. A method of imaging or in vivo diagnosis which comprises administering to a patient a compound of formula (I) according to claim 1 and detecting the location of said compound in said patient.

17. A method of evaluation of the effects of the administration of a drug to an animal or human suffering from a pathology during which neovascularization occurs which comprises successively
 a) administering a compound of formula (I) according to claim 1 to said patient and detecting the location of said compound;
 b) administering said drug to said patient;
 c) administering said compound to said patient again and detecting the location of said compound; and
 d) comparing the location of the said compound in step a) with the location of said compound in step c).

\* \* \* \* \*